United States Patent [19]

Evans

[11] Patent Number: 4,665,055

[45] Date of Patent: May 12, 1987

[54] PEPTIDE RENIN INHIBITORS

[75] Inventor: Ben E. Evans, Lansdale, Pa.

[73] Assignee: Merck & Co., Inc., Rahway, N.J.

[21] Appl. No.: 745,560

[22] Filed: Jun. 17, 1985

[51] Int. Cl.[4] .................... A61K 37/43; C07K 5/08
[52] U.S. Cl. ..................................... 514/18; 530/331
[58] Field of Search ................ 260/112.5 R; 514/18; 530/331

[56] References Cited

U.S. PATENT DOCUMENTS

| | | | |
|---|---|---|---|
| 3,784,686 | 1/1974 | Miller | 424/94 |
| 3,873,681 | 3/1975 | Miller | 424/9 |
| 4,384,994 | 5/1983 | Veber et al. | 530/330 |
| 4,397,786 | 8/1983 | Evans et al. | 260/404 |

FOREIGN PATENT DOCUMENTS 0045665  2/1982  European Pat. Off. .
0077,029  4/1983  European Pat. Off. .

OTHER PUBLICATIONS

J. Org. Chem. (1985) 50, 4615–25.
K. E. Rittle, et al., J. Org. Chem. 47 3016 (1982).
Boger, et al. *Nature* 303: 81–84 (1983).
Holladay & Rich, *Tetrahedron Lett.*, 24, 4401 (1983).
*Proceedings of the American Peptide Symposium*, (1983) 579, Szekle et al.
Corey, E. J. et al., *J. Am. Chem. Soc.*, 87 1353 (1965).
Corey et al., *J. Am. Chem. Soc.*, 94 6190 (1972).

*Primary Examiner*—Delbert R. Phillips
*Attorney, Agent, or Firm*—Richard A. Elder; Hesna J. Pfeiffer

[57] ABSTRACT

Peptides having the formula:

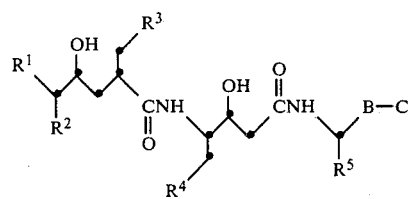

and their use as pharmaceuticals are disclosed. Also disclosed is a process for synthesis of the 4-hydroxyacyl unit of the formula:

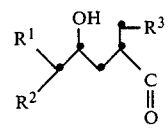

13 Claims, No Drawings

PEPTIDE RENIN INHIBITORS

BACKGROUND OF THE INVENTION

The invention is concerned with novel peptide renin inhibitors and synthesis of intermediate 4-hydroxyacyl units.

Peptide renin inhibitors are disclosed in the literature [See e.g. U.S. Pat. No. 4,384,994; European Patent Application No. 0,077,029; U.S. Pat. No. 4,397,786; Boger et al. *Nature* 303: 81–84 (1983)]. One class of such inhibitors contains the statine type amino acid residue of the formula:

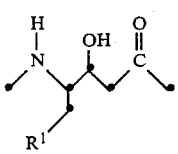

which is (3S,4S)-4-amino-3-hydroxy-6-methylheptanoic acid and its analogs.

Peptide renin inhibitors have been discovered containing a 4-hydroxyacyl group of the formula:

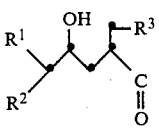

attached to the nitrogen of the statine type amino acid. Synthesis of specific examples of this 4-hydroxyacyl group where $R^1$ is nitrogen have been described in the literature (see e.g. European Patent Application EP45665; Holladay and Rich, *Tetrahedron Lett.*, 1983, 24, 4401; Szelke et al., *Proceedings of the American Peptide Symposium* (8th), 1983, 579). These synthesis do not provide easy access to all individual diastereomers nor do they provide compatability with a wide range of substituents $R^2$ and $R^3$. A new stereocontrolled synthesis of this 4-hydroxyacyl group which does provide these features has been discovered.

SUMMARY OF THE INVENTION

A peptide compound having the formula

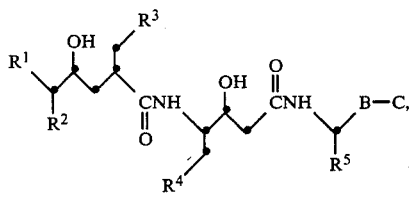

intermediates, and a process.

DETAILED DESCRIPTION OF THE INVENTION

An embodiment of the present invention is a peptide compound of the formula:

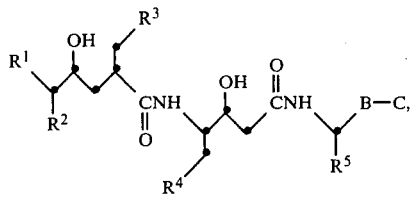

and pharmaceutically acceptable salts thereof wherein
(i) $R^1$ is A—B'—B'—D'—NH.
wherein
A is hydrogen;

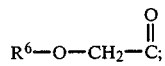

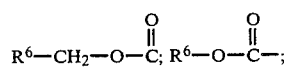

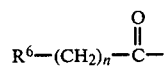

wherein n is 0–5; or

where $R^6$ is hydrogen; $C_{3-6}$ alkyl; $C_{3-7}$ cycloalyl; phenyl; or phenyl mono-substituted with a member selected from the group consisting of methyl, trifluoromethyl, hydroxy, methoxy, fluoro, chloro, bromo, and iodo;

B' is absent; glycyl; or

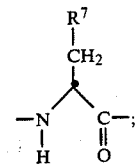

D' is absent; or

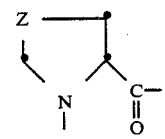

where Z is $(CH_2)_n$ and n is 1 or 2; or —S—; and
$R^7$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl; and
$R^2$ is $CH_2R^8$;
wherein $R^8$ is hydrogen; $C_{1-4}$ alkyl; phenyl; phenyl mono-substituted with a member selected from the group consisting of methyl, trifluoromethyl, hydroxy, methoxy, fluoro, chloro, bromo, and iodo; or indolyl; and (ii)
R¹ and R² are the same or different and are hydrogen; Y—(CH₂)ₙ— or Y—(CH₂)ₘ—CH=CH—(CH₂)ₚ— where Y is hydrogen; aryl; aryl substituted with up to five members independently selected from the group consisting of $C_{1-8}$alkyl, trifluoromethyl, hydroxy, $C_{1-4}$alkoxy, and halo; n is 0 to 5; m is 0 to 2; and p is 0 to 2; and R³ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl;

R⁴ is $C_1$–$C_4$ branched or linear alkyl, $C_3$–$C_6$ cycloalkyl, phenyl or mono-substituted phenyl wherein the substituent is OH, Cl, F, Br, CH₃, CF₃, I or OCH₃;

R⁵ is hydrogen or

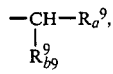

wherein $R_a^9$ and $R_b^9$ are independently selected from hydrogen, $C_1$–$C_4$ alkyl, hydroxy, phenyl or $C_3$–$C_7$ cycloalkyl;

B-C is

wherein R¹⁰ is selected from:
(a)

B''        V wherein
B'' is OR; NHR; or NR², where each R may be the same or different and is hydrogen or $C_{1-4}$ alkyl;
(b)

B''—E      VI wherein
B'' is absent; glycyl; or

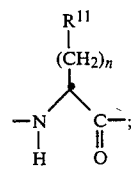

wherein n is 1 or 2; or —S—;
R¹¹ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl; and
E is OR; NHR, or N(R)₂, where each R may be the same or different and is hydrogen or $C_{1-4}$ alkyl; and
(c)

B°—D—E      VII wherein
B° is
(1) —Y—(CH₂)ₙ—R¹² where Y is —NH— or —O—; n is 0 to 5; and R¹² is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di-$C_{1-4}$ alkylamino, and halo; amino; mono-, di-, or tri-$C_{1-4}$alkylamino; guanidyl; heterocyclic; or hetertocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino;

(2)

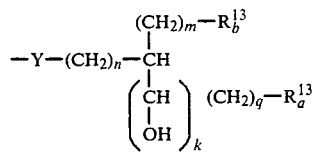

wherein Y is as defined above; n is 0 or 1; k is 0 or 1; q is 1 to 4; m is 1 to 4; and $R_a^{13}$ and $R_b^{13}$ may be the same or different and have the same meaning as R¹² above and $R_a^{13}$ may additionally be

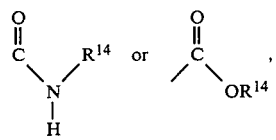

where R¹⁴ is hydrogen or $C_{1-3}$alkyl;
(3)

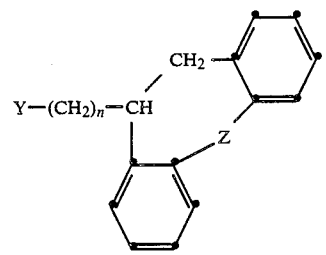

where Y is as defined above; n is 0 or 1; and Z is
(a)

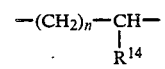

where n is 0 or 1; and R¹⁴ is as defined above; or
(b)

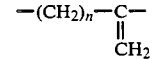

where n is 0 or 1; or
(4)

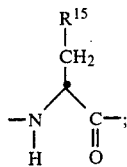

wherein R¹⁵ has the same meaning as R⁴ above,
D is absent; glycyl; sarcosyl; or

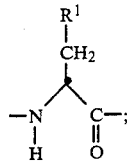

and
E is absent; OR; NHR; or N(R)₂ where R may be the same or different and is hydrogen or $C_{1-4}$alkyl; or (d)

 —E—   VIII wherein:
E is
(1) —Y—(CH₂)ₙ—R¹⁶ where Y is —NH— or —O—; n is 0 to 5; and R¹⁶ is hydrogen; $C_{1-3}$alkyl; $C_{3-7}$cycloalkyl; naphthyl; phenyl; phenyl substituted with up to five members independently selected from the group consisting of methyl, trifluoromethyl, hydroxyl, methoxy, amino, fluoro, chloro, bromo, and iodo; imidazolyl; pyridyl; pyrryl; hydroxyl; amino; $C_{1-4}$alkyl mono-, di-, or tri-substituted amino; guanidyl; piperidyl; tetrahydropyrryl; or N-substituted piperidyl or tetrahydropyrryl where the N-substituent is a member selected from the group consisting of hydrogen, $C_{1-6}$alkyl, $C_{1-6}$hydroxyalkyl, phenyl, benzyl, naphthyl, and naphthylmethyl;

(2)

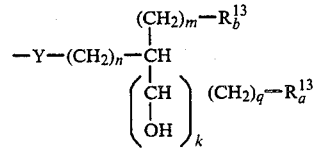

where Y is as defined above; n is 0 or 1; k is 0 or 1; q is 1 to 4; m is 1 to 4; and $R_a^{13}$ and $R_b^{13}$ may be the same or different and have the same meaning as R¹⁶ above; or (3)

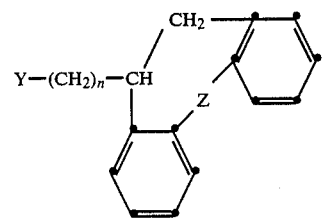

where Y is as defined above; n is 0 or 1; and Z is (a)

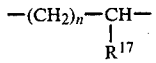

where n is 0 or 1; and R¹⁷ is hydrogen or $C_{1-3}$alkyl; or (b)

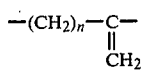

where n is 0 or 1.

The pharmaceutically acceptable salts of Formula I compounds include those derived from inorganic or organic acids as well as quaternary salts. Included among such acid derived salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, isethionate, lactate, maleate, methanesulfonate, 2-naphthalenesulfonate, nicotinate, oxalate, pamoate, phosphate, pectinate, persulfate, 3-phenylpropionate, picrate, pivalate, propionate, succinate, tartrate, thiocyanate, tosylate, undecanoate. Also, the basic nitrogen-containing groups can be quaternized with such agents as lower alkyl halide, such as methyl, ethyl, propyl, and butyl chloride, bromides and iodides; and diamyl sulfates, long chain halides such as decyl, lauryl, myristyl and stearyl chlorides, bromides and iodides, aralkyl halides like benzyl and phenethyl bromides and others.

The peptides of Formula I are characterized by containing a unit of the formula II:

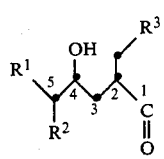   II wherein R¹, R² and R³ are defined as above. Preferred definition of R¹ is acylamino; especially preferred definitions are t-butyloxycarbonylamino and phenoxyacetylamino. Preferred definitions of R² are C₁-C₆ alkyl and aralkyl;-especially preferred R² is benzyl. Preferred definitions of R³ are C₁-C₆ alkyl, aryl and heteroaryl; especially preferred R³ are phenyl and 4-imidazolyl. Preferred sterochemistry at C₂ of formula II is R or S, at C₄ is R or S and at C₅ is S.

Preferred compounds of formula I are:
(a)   Nα-[5-(t-BOC-amino)-4-hydroxy-6-phenyl-2-(phenylmethyl)hexanoyl]-(3S,4S)-4-amino-5-cyclohexyl-3-hydroxypentanoyl-L-leucyl-m-aminomethylbenzyl-amide, and
(b)   Nα-[5-(t-BOC-amino)-4-hydroxy-6-phenyl-2-(phenylmethyl)hexanoyl]-(3S,4S)-statyl-L-leucinebenzylamide.

More preferred compounds are compounds having the following configurations in the formula II unit:
the (a) compounds having the 2R,4S,5S configuration;
the (a) compounds having the 2S,4S,5S configuration;

the (a) compounds having the 2R,4R,5S configuration;
the (a) compounds having the 2S,4R,5S configuration;
the (b) compounds having the 2R,4R,5S configuration;
the (b) compounds having the 2S,4R,5S configuration;
the (b) compounds having the 2R,4S,5S configuration;
the (b) compounds having the 2S,4S,5S configuration;

Another embodiment of the present invention is a pharmaceutical composition containing a renin-inhibitory amount of a compound of formula I or pharmaceutically acceptable salt thereof. The composition, may, if required, be formulated using conventional carriers diluents, excipients and the like.

The formula I peptides possess activity in treating renin-associated hypertension and hyperaldosteronism.

For these purposes the compounds of the present invention may be administered parenterally, by inhalation spray, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer3 s solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The peptides of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Another embodiment of the present invention is a method of treating renin-associated hypertension and hyperaldosteronism, comprising administering to a patient in need of such treatment, a therapeutically effective amount of a peptide of formula I or a pharmaceutically acceptable salt thereof.

The renin inhibitory peptides of the present invention may also be utilized in diagnostic methods for the purpose of establishing the significance of renin as a causative or contributory factor in hypertension or hyperaldosteronism in a particular patient. For this purpose the peptides of the present invention may be administered in a single dose of from 0.1 to 10 mg per kg of body weight.

Both in vivo and in vitro methods may be employed. In the in vivo method, a novel peptide of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel peptide of the present invention, and after deproteinization, measuring the amount of angiotensin II produced in nephrectomized, pentolinium-treated rats. Another in vitro method involves mixing the plasma or other body fluid with a novel peptide of the present invention and injecting the mixture into a test animal. The difference in pressor response with and without added peptide is a measure of the renin content of the plasma.

Pepstatin may be employed in the methods described above as an active control. See, e.g., U.S. Pat. Nos. 3,784,686 and 3,873,681 for a description of the use of pepstatin in diagnostic methods of this type.

The peptides of the present invention may be prepared by using any convenient method. An especially useful method utilizes chiral aminoalkyl epoxides.

Abbreviated designations for amino acid components, certain preferred protecting groups, reagents, solvents, etc. which may be used herein are given below:

| Abbreviated Designation | |
|---|---|
| | Amino Acid |
| ACHPA | (3S,4S)—4-amino-5-cyclohexyl-3-hydroxypentanoic acid |
| Leu | L-leucine |
| Phe | L-phenylalanine |
| Sta | (3S,4S)—statine |
| | Protecting Groups |
| BOC | tert-butyloxycarbonyl |
| CBZ | benzyloxycarbonyl |
| OMe | methyl ester |
| | Activating Groups |
| HBT | 1-hydroxybenzotriazole |
| ONp | p-nitrophenyl |
| | Condensing Agents |
| DCC | dicyclohexylcarbodiimide |
| DPPA | diphenylphosphorylazide |
| EDC | 1-ethyl-3-(3-dimethylaminopropyl)-carbodiimide hydrochloride |
| | Reagents |
| Et₃N | triethylamine |

| Abbreviated Designation | |
|---|---|
| TFA | trifluoroacetic acid |
| POA | phenoxyacetyl |
| IBU | isobutyryl |
| TBDMSCl | t-butyldimethylsilyl chloride |
| $Bu_4B^+F^-$ | tetra-n-butylammonium fluoride |
| Im | imidazole |
| PMA | phosphomolyldic acid, ethanol solution, for TLC visualization |
| Solvents | |
| HOAc | acetic acid |
| $CHCl_3$ | chloroform |
| DMF | dimethylformamide |
| DMSO | dimethylsulfoxide |
| EtOAc | ethyl acetate |
| MeOH | methanol |
| THF | tetrahydrofuran |

Another embodiment of the present invention is a preferred method for preparing the segments of formula II for inclusion in compounds of formula 1. This method is illustrated by the following reaction schemes. All stereoisomers of the compounds of formulae 2-11-, 13, 16-25, 27-30, and 32, and the method of chiral purity determination of intermediate epoxides by formation of carbinolamines 34a, as shown in Scheme 5, are other embodiments of the invention.

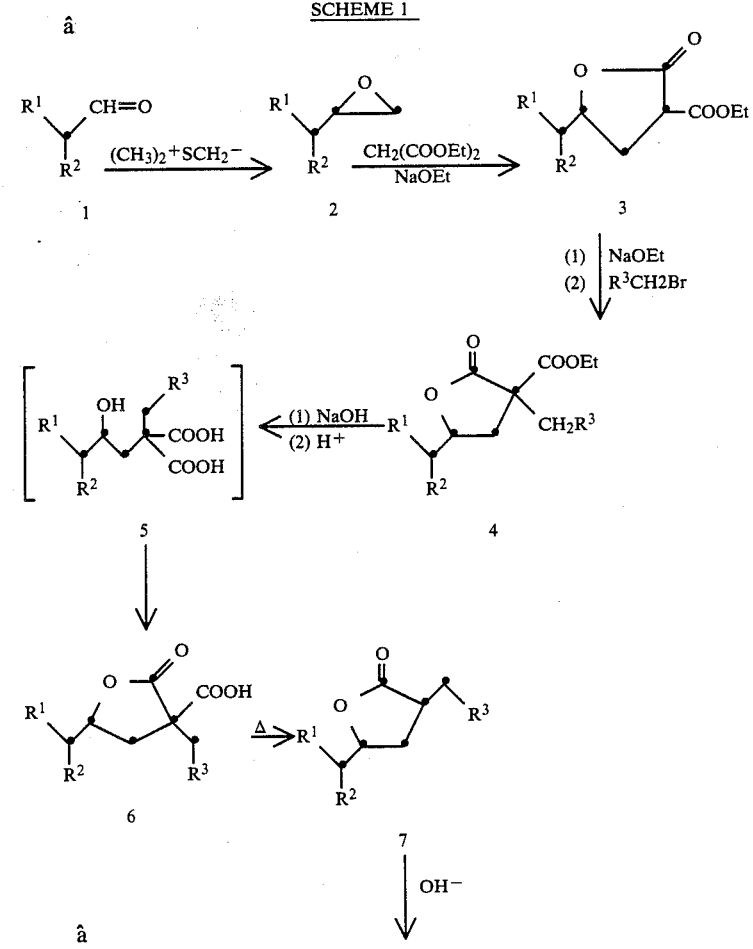

SCHEME 1

-continued
SCHEME 1
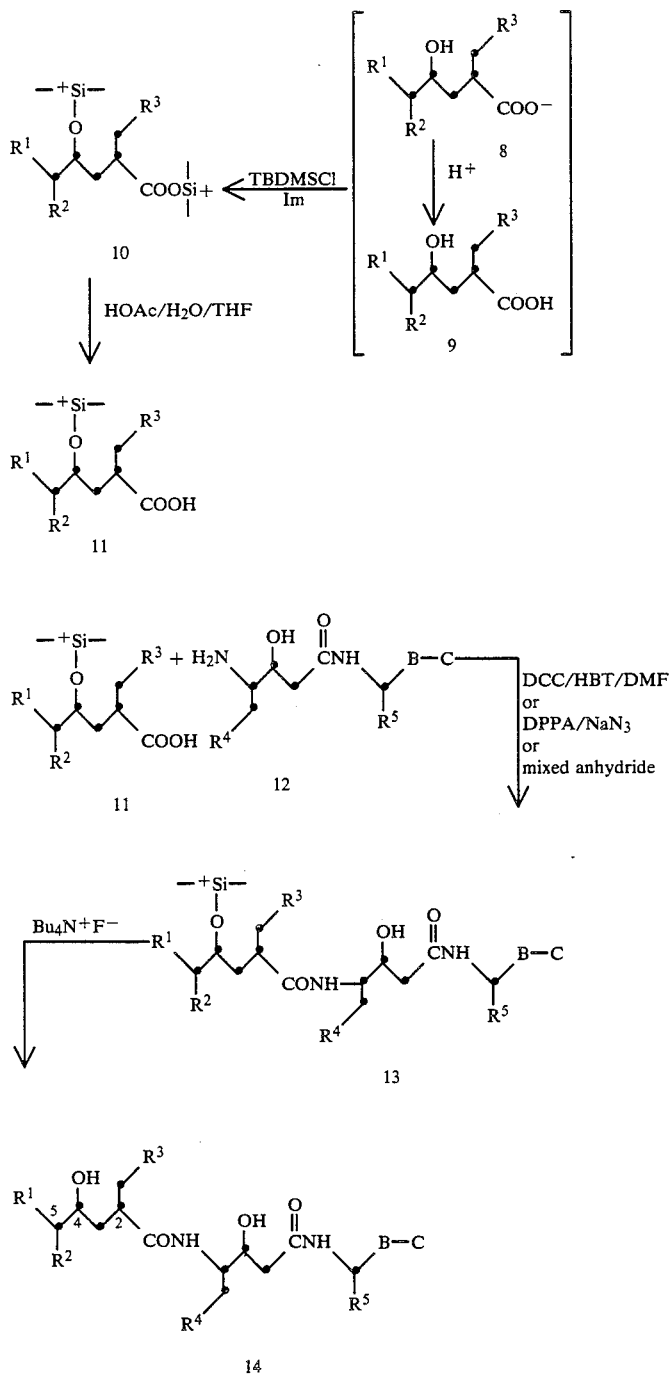

SCHEME 2
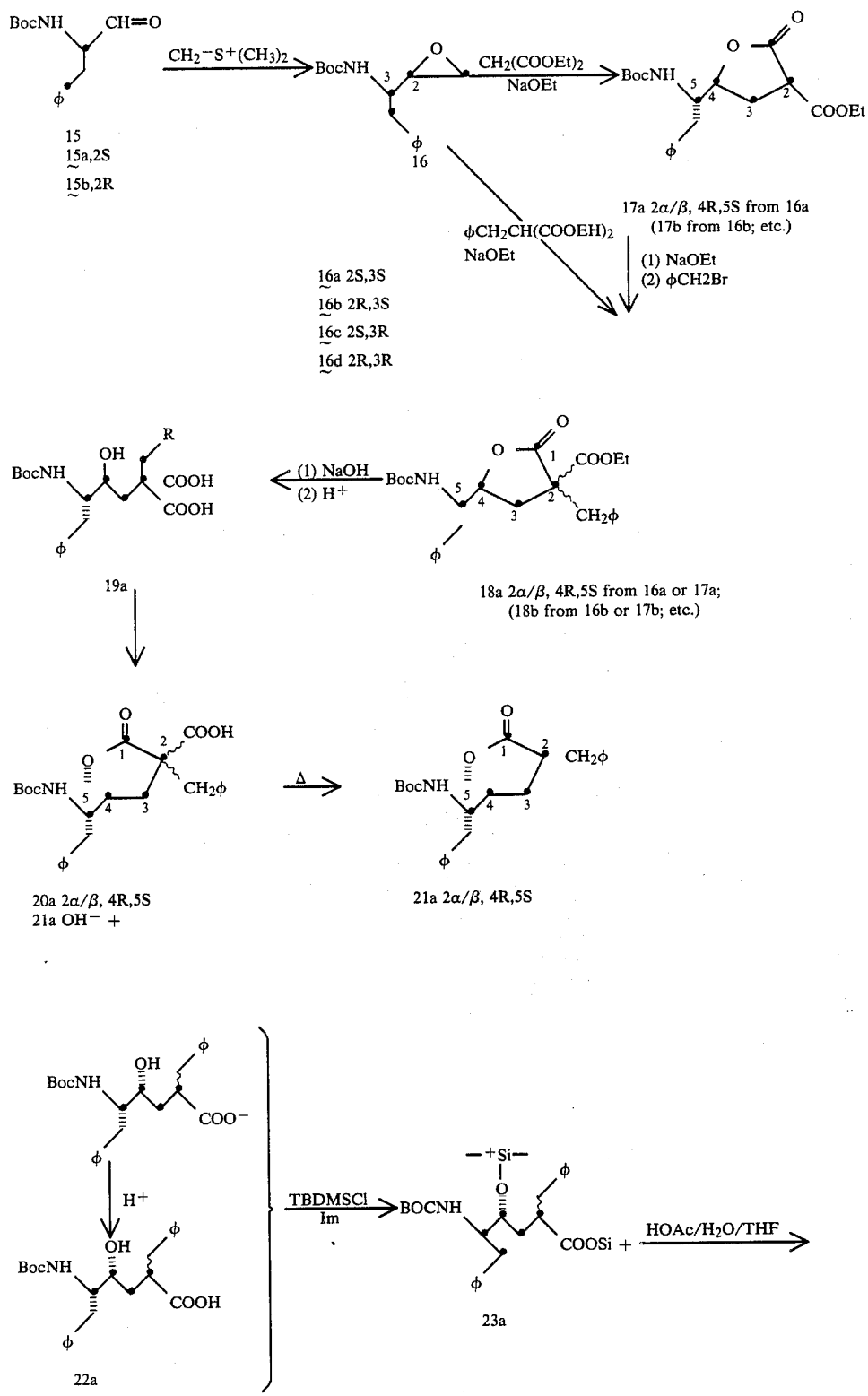

-continued
SCHEME 2
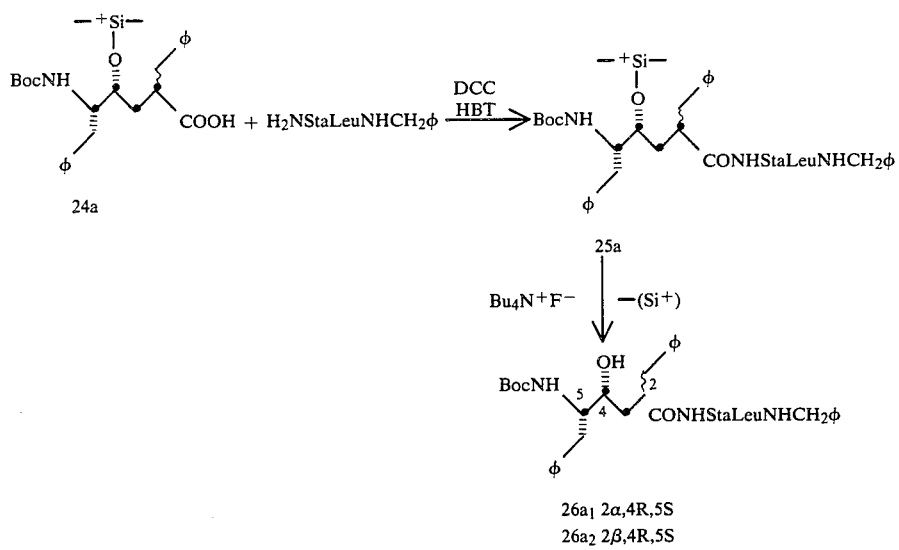
SCHEME 3
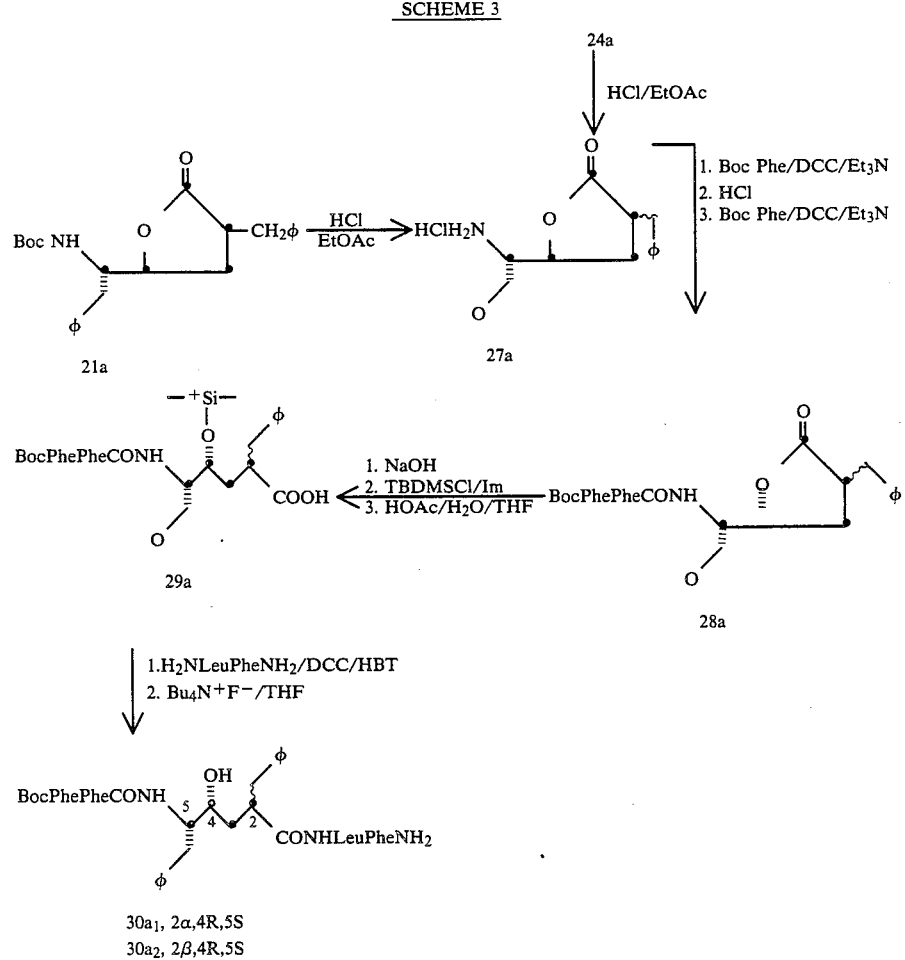

SCHEME 4

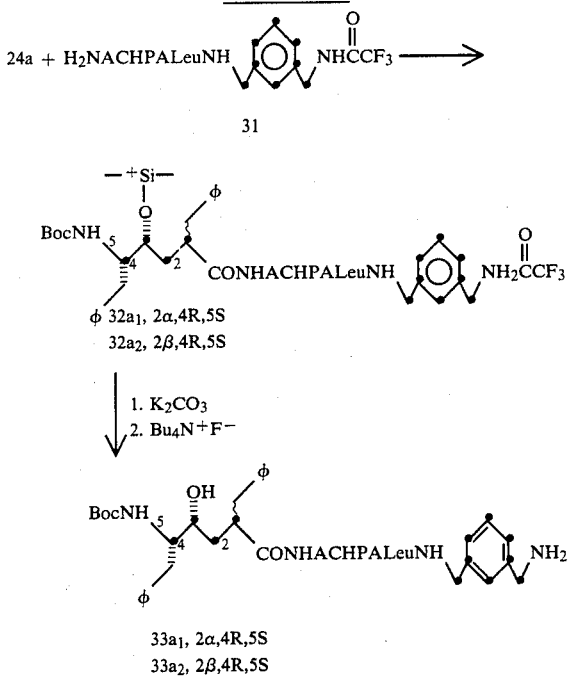

SCHEME 5

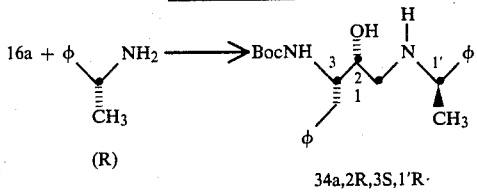

phy. HPLC (high performance liquid chromatography) may also be utilized for these separations.

Examples of this approach are shown in Schemes 2 and 3. In Scheme 2, the aldehyde 15a or 15b, obtained from Boc-L-phenylalanine or Boc-D-phenylalanine according to published methods,[3] is converted to epoxide 16 as described above. From 15a, the isomers 16a and 16b are obtained and these are separated by silica gel chromatography. Each of the four epoxides 16a, b, c, or d may be carried through the sequence of Schemes 2–4; the present examples are illustrated for 16a. Thus, 16a alkylates diethylmalonate to provide 17a as a mixture of two isomers (at $C_2$). These may be used without separation. Alkylation with benzyl bromide then gives 18a, and saponification followed by relactonization provides 20a. Thermal decarboxylation to 21a followed by lactone opening, silation, and selective desilation as described above provides acid 24a. Coupling to Sta-LeuNHCH$_2\phi$ by conventional methodology (DCC/HBT), followed by desilation provides the peptide 26a as a mixture of two isomers ($a_1$ and $a_2$, at $C_2$) Tnese are separated by silica gel chromatography.

[3] Rittle, K. E., Homnick, C. F., Ponticello, G. S., and Evans, B. E., J. Org. Chem. 47 3016 (1982).

In cases where further elaboration in the N-terminus of peptides such as 26 is required, a modified approach is taken, as illustrated in Scheme 3. Here, the lactone 21a is N-deprotected with HCl in ethyl acetate to give 27a. 27a may also be obtained from 24a by similar acid treatment. 27a may be elaborated on the free amino group by conventional acylation or peptide coupling. In the example of Scheme 3, two couplings with BocPhe with an intervening deprotection provides the Boc-PhePhe derivative 28a. Ring opening-silation-selective desilation as before now gives the acid 29a which, when coupled to the desired C-terminal fragment, in this case LeuPheNH2, and desilated, gives the product 30a as a mixture of two diastereomers ($a_1$ and $a_2$, at $C_2$) Separation is achieved by silica gel chromatography.

In an additional example (Scheme 4), the acid 24a is coupled to ACHPA-Leu-m-trifluoroacetylaminomethylbenzylamide (31) to give the protected peptides 32. Removal of the trifluoroacetyl and t-butyldimethylsilyl protecting groups gives the peptide 33a as a mixture of diastereomers. These are separated by preparative HPLC.

In the examples shown in Schemes 2–4, the absolute configuration at $C_5$ of the final product (26a, 30a, and 33a) is determined by the configuration at $C_3$ of the epoxide 16a. This is established by the choice of the amino acid in the synthesis of 15 (Boc-L-Phe for 16a). Chiral purity is verified by reacting one diastereomer of the resulting epoxide (i.e., 16a) with d(+)-(R)-α-methylbenzylamine and measuring the diastereomeric purity of the resulting carbinolamine 34a, (Scheme 5).

Following are examples illustrating preparation of compounds of the present invention. All temperatures are in degrees Celsius unless otherwise indicated. The numbering of carbon skeletons in these example titles reflects standard nomenclatural practice. The resulting numberings do not necessarily coincide with the reference numbers appearing in the schemes and referred to above for designation of stereochemistry. Designation of a stereocenter as α indicates a single isomer of undetermined absolute stereochemistry. The designation β indicates the single isomer of the opposite configuration.

Referring to Scheme 1, aldehydes of structure 1 are converted to the epoxides 2 with dimethylsulfinylcarbanion.[1] Alkylation of malonic ester with 2 gives the lactohes 3, and alkylation of these compounds with alkyl halides $R^3CH_2X$ provides the alkyl compounds 4. Sodium hydroxide cleaves the ethyl ester, and also opens the lactone ring to give, after acidification, the diacids 5 which, upon standing, reclose to lactone 6. Upon controlled heating, 6 is decarboxylated to 7, which is converted to the open-chain acid 9 by treatment with sodium hydroxide followed by acidification. 9, or its salt 8, with t-butyldimethylsilyl chloride and imidazole, gives the disilated compound 10 which is selectively monodesilated with acetic acid in aqueous THF according to the procedure of Corey and Venkateswarlu.[2] The resulting silylether 11 is coupled to free peptide N-termini such as in 12 to give the peptides 13. These are deprotected using tetrabutylammonium fluoride giving the final products 14.

[1] Corey, E. J. and Chaykovsky, M., J. Am. Chem. Soc. 87 1353 (1965).
[2] Corey, E. J. and Venkateswarlu, A., J. Am. Chem. Soc. 94 6190 (1972)

Three chiral centers at $C_2$, $C_4$, and $C_5$ in 14 provide eight possible stereoisomers. The stereochemistry at $C_5$ is established by the stereochemistry of the starting aldehyde 1. Stereochemistry at $C_4$ is selected by an isomer separation at either the epoxide (2) or lactone (3) intermediate. Stereochemistry at $C_2$ is selected by separation of the final products 14. Separations are most conveniently carried out using silica gel chromatogra-

EXAMPLE 1

1-(1-Boc-amino-2-phenylethyl)oxirane (16)

Boc-L-phenylalanine (25 g, 0.1 mol) was reduced to the carbinol and re-oxidized to the aldehyde 15a using the procedures previously described.[3] The crude aldehyde was used immediately, without purification.

Dimethylsulfonium methylide (210 mmol) was prepared in DMSO/THF according to the procedure of Corey and Chaykovsky.[1] After stirring for 1 minute at −5° C., the mixture was treated with the crude aldehyde dissolved in THF (135 mL), added fairly rapidly. The resulting mixture was stirred in the cold for 30 minutes, then quenched in cold $H_2O$ (3 L). The suspension was extracted with ether (3×100 mL) and the combined organic layers were washed with $H_2O$ (2×100 mL), dried over $Na_2SO_4$, filtered, and evaporated to dryness in vacuo. The product was chromatographed on silica gel eluted with 3:1 (v/v) hexane:ethyl acetate. Evaporation of the product fractions in vacuo gave the mixed epoxides 16a and b as a white solid. The ratio of 16a to 16b as determined by the relative intensities of the protons at 3.7 and 4.1δ (see below) was ca. 1:1. This material was used in subsequent reactions without further refinement.

16a. A sample of the mixture was crystallized from ether by addition of petroleum ether (10 x), and the resulting solid recrystallized from hexane to give 16a: mp 121.5°–123.5° C.

$^1$H NMR: consistent with title structure, $C_2H$ at 3.7δ.

TLC: single component, $R_f$=0.53, silica gel plate, 2:1 (v/v) hexane:ethyl acetate elution HPLC: 97.5% (contains 2.5% 16b)

Anal. Calc'd for $C_{15}H_{21}NO_3$: C, 68.41; H, 8.04; N, 5.32. Found: C, 68.25; H, 8.31; N, 5.37.

16b. The petroleum ether/ether recrystallization filtrate was evaporated to dryness in vacuo and the residue recrystallized twice from ether to give a mixture of 16a and 16b in which 16b was dominent (70%): mp 85°–89° C.

$^1$H NMR: consistent with title structure, $C_2H$ at 4.1 δ and 3.7 δ, 70:30.

TLC: single component, $R_f$=0.53, identical to 16a, silica gel plate, 2:1 (v/v) hexane:ethyl acetate elution.

Anal. Calc'd for $C_{15}H_{21}NO_3$: C, 68.41; H, 8.04; N, 5.32. Found: C, 68.15; H, 8.16; N, 5.63.

Repeated crystallization provided homogeneous 16b as an oil, NMR $C_2H$ at 4.1 δ.

16b+c. Racemic aldehyde 15a/b was prepared from Boc-DL-phenylalanine and converted to the epoxide mixture 16a-d using the procedures described above. The chromatographed product was evaporated to an oil which deposited a diastereomer mixture (1:1) from ether:hexane (1:10). The filtrate was evaporated, redissolved in ether:hexane and boiled gently to remove the bulk of the ether. After removal of a second mixed diastereomer crop (16+d:16b+c=5:1) by filtration, the filtrate deposited a final portion consisting of one (16b+c) racemate (m.p. 94°–97.5° C.).

Single crystal X-ray analysis revealed a structure with R configuration at the substituted epoxide carbon and S configuration at carbon α to nitrogen.

$^1$H NMR: consistent with structure, $C_2H$ at 4.1 δ.

16a+d. Recrystallization of the 5:1 mixed isomer from hexane provided the other racemate 16a+d: m.p. 101°–102.5° C.

$^1$H NMR: consistent with structure, $C_2H$ at 3.7 δ.

EXAMPLE 2

5-(1-t-Boc-amino-2-phenylethyl)-3-carboethoxydihydrofuran-2(3H)-one (17)

Epoxide 16 (mixed isomers a+b, 21.9 g, 83 mmol) and diethyl malonate (16 g, 100 mmol) were combined in 60 mL of dry ethanol. The solution was stirred in an ice bath under nitrogen and treated with a solution of sodium ethoxide (prepared from 1.84 g, 80 mmol of metallic sodium and 31 mL of dry ethanol), added dropwise. The mixture was stirred overnight at room temperature. (In cases where TLC indicated the reaction was not complete, an extra 10% diethyl malonate was added and the mixture heated in an oil bath thermostatted at 50° C. for 2 hours.) The solution was quenched in 200 mL of cold $H_2O$ containing 5 g of citric acid. The mixture was extracted with ether (4×70 mL) and the combined ether layers were washed with $H_2O$, dried over sodium sulfate, filtered, and evaporated to dryness in vacuo. The residue was separated and purified by chromatography on silica gel (750 g, 230–400 mesh, 55 mm id column, medium pressure, 6:1→3:1 (v/v) hexane:ethyl acetate elution). The product fractions were evaporated in vacuo to give the 4R,5S lactone 17a and the 4S,5S isomer 17b, each as a white solid homogeneous to TLC (silica gel GF, 3:1 (v/v) hexane:ethyl acetate). Samples of each were recrystallized from hexane/ethyl acetate (10:1).

17b. m.p. 104°–106° C.

$^1$H NMR: consistent with title structure.

Anal. Calc'd for $C_{20}H_{27}NO_6$: C, 63.64; H, 7.21; N, 3.71. Found: C, 63.57; H, 7.32; N, 3.40.

17a. m.p. 103°–104° C.

$^1$H NMR: consistent with title structure.

Anal. Calc'd for $C_{20}H_{27}NO_6$: C, 63.64; H, 7.21; N, 3.71. Found: C, 63.65; H, 7.40; N, 3.77.

The isomers 17a and 17b were each homogeneous by TLC (3.1 hexane/ethyl acetate, silica gel) and were distinguishable from one other (17a; $R_f$=0.23; 17b; $R_f$=0.27). The absolute configurations were established by comparison with pure samples of 17a and 17b prepared from the separated epoxides 16a and 16b, respectively, by the procedure described above.

EXAMPLE 3

5-(1-t-Boc-amino-2-phenylethyl)-3-carboethoxy-3-phenylmethyldihydrofuran-2(3H)-one (18)

18a. Lactone 17a (0.1 g, 0.26 mmol) in dry ethanol (0.5 mL, distilled from sodium ethoxide) was treated with sodium ethoxide (0.1 mL of a 2.5 M solution in ethanol, 0.25 mmol) followed by benzyl bromide (0.044 g, 0.26 mmmol) and the mixture stirred under nitrogen in an oil bath thermostatted at 50° C. Periodic TLC assay (3:1 hexane:ethyl acetate, silica gel) indicated the reaction was complete after 1 hour. At this time, the mixture was cooled, quenched in cold, dilute citric acid solution (10 mL), and extracted with ether (2×10 mL). The combined ether layers were washed with $H_2O$, dried over sodium sulfate, filtered, and evaporated to dryness in vacuo to give the lactone 18a as a white foam.

A sample of this material, chromatographed on silica gel (3:1 hexane:ethyl acetate) to remove a trace of a baseline contaminant, was obtained as a sticky solid.

$^1$H NMR consistent with structure.

TLC: two diastereomers, $R_f$=0.36 and 0.39, silica gel plate, 3:1 hexane:ethyl acetate elution.

Anal. Calc'd for $C_{27}H_{33}NO_6$: C, 69.36; H, 7.11; N, 3.00. Found: C, 69.53; H, 7.43; N, 3.09.

18b. Lactone 17b was alkylated with benzyl bromide as described in the preparation of 18a. A chromatographed sample of 18b was obtained as a sticky solid.

$^1$H NMR consistent with structure.

TLC single component, $R_f=0.46$, silica gel plate, 3:1 hexane:ethyl acetate elution.

Anal. Calc'd for $C_{27}H_{33}NO_6$: C, 69.36; H, 7.11; N, 3.00. Found: C, 69.32; H, 7.23; N, 3.03

EXAMPLE 4

5-(1-t-Boc-Amino-2-phenylethyl)-3-phenylmethyldihydrofuran-2(3H)-one (21)

21b. Lactone 18b (3.3 g, 7.1 mmol) in dioxane (60 mL) was diluted with $H_2O$ (60 mL) and stirred in an open vessel. The pH of the mixture was monitored with a pH meter standardized with a 1:1 mixture of dioxane and pH 10 buffer. Sodium hydroxide (14 mL of 1N solution, 14 mmol) was added dropwise, the pH rising to ca. 12.5. After 3 hours the mixture was evaporated in vacuo to remove the bulk of the dioxane, then washed twice with ether. The aqueous phase was acidified to pH~2 with 1N HCl and extracted with ether (3×50 mL). The combined ether layers were washed with $H_2O$, dried over sodium sulfate, filtered, and evaporated in vacuo to give 20b as a sticky solid.

$^1$H NMR consistent with structure.

Thermogravimetric analysis (TGA) indicated that 20b underwent a single thermal process corresponding to loss of $CO_2$ in the region 100°–130° C. Acid 20b (1.0 g, 2.3 mmol) was heated under a nitrogen stream in a flask immersed in an oil bath thermostatted at 120° C. After 30 minutes, TLC (80:10:1 $CH_2Cl_2$:MeOH:HOAc, silica gel plate) indicated complete conversion of the acid to a higher $R_f$ material. Following chromatography on silica gel ($CH_2Cl_2$ and 1% MeOH in $CH_2Cl_2$) to remove a trace of a baseline component, the product fractions were evaporated in vacuo to give 21b as a colorless oil.

$^1$H NMR consistent with structure.

TLC: single component, $R_f=0.51$, silica gel plate, 1% (v/v) MeOH in $CH_2Cl_2$ elution.

Anal. Calc'd for $C_{24}H_{29}NO_4$. 0.05 $CH_2Cl_2$: C, 72.25; H, 7.33; N, 3.50. Found: C, 72.29; H, 7.52; N, 3.62.

21a. Lactone 18a (3.3 g, 7.1 mol) was converted to the lactone acid 20a as described for the isomer 20b. The product was obtained as a colorless oil.

$^1$H NMR consistent with structure.

Decarboxylation of 20a (1.0 g, 2.3 mmol) as described for 20b and crystallization of the chromatographed product from ether gave 21a as a white solid.

$^1$H NMR consistent with structure.

TLC (1% (v/v) MeOH/$CH_2Cl_2$) single component, $R_f=0.45$.

Anal. Calc'd for $C_{24}H_{29}NO_4$: C, 72.88; H, 7.39; N, 3.54. Found: C, 73.11; H, 7.62; N, 3.72.

EXAMPLE 5

5-(t-Boc-amino)-4-(t-butyldimethylsilyloxy)-6-phenyl-2-phenylmethylhexanoic acid (24).

24a. Lactone 21a (6.95 g, 17.6 mmol), stirred in a mixture of dioxane (100 mL) and $H_2O$ (50 mL), was treated with sodium hydroxide (19.3 mL, 1 M, 19.3 mmol) added dropwise over 5 minutes. The mixture was stirred briskly for 30 minutes and the bulk of the dioxane removed in vacuo. The remaining mixture was acidified to pH 2 with 10% citric acid, and extracted with ether (3×30 mL). The combined ether layers were washed with $H_2O$, dried over sodium sulfate, filtered and evaporated to dryness in vacuo. The residue was triturated with petroleum ether to yield 22a as a white solid. This material was found to revert to the lactone 21a at a detectable rate (10–20% by TLC after 41 days at 0° C., solid phase; considerably faster in solution at ambient temperature) and was therefore immediately silated upon isolation.

22a. (7.3 g, 17.7 mmol), t-butyldimethylsilyl chloride (13.3 g, 87.9 mmol) and imidazole (11.4 g, 168 mmol) were combined in dry DMF (34 mL) and stirred at room temperature under nitrogen for 18 hours. The mixture was evaporated in vacuo and the residue treated with ice $H_2O$. The resulting mixture was acidified to pH~4 with 10% citric acid and extracted with ether (3×60 mL). The combined ether layers were washed with $H_2O$, dried over sodium sulfate, filtered and evaporated in vacuo to give the silyl ether-silyl ester 23a as a colorless syrup. This material was dissolved in a mixture of THF (76 mL), glacial acetic acid (76 mL) and $H_2O$ (25 mL) according to the procedure of Corey and Venkateswarlu,[2] stirred 1.5 hours at ambient temperature, and refrigerated overnight. After an additional 1 hour at ambient temperature, TLC (2% MeOH/$CH_2Cl_2$, silica gel) indicated the reaction was complete. The mixture was evaporated in vacuo and the residue diluted with $H_2O$ (60 mL) and extracted with ether (3×50 mL). The combined ether layers were dried over sodium sulfate, filtered, and evaporated to dryness in vacuo. The residue was chromatographed on silica gel (500 g) eluted with a gradient of 0–3% MeOH in $CH_2Cl_2$ to give the product silyl acid 24a, as a white solid, along with some recovered lactone 21a. 24a: $^1$H NMR: consistent with structure.

TLC: (4% (v/v) MeOH/$CH_2Cl_2$) single component, $R_f=0.56$.

Anal. Calc'd for $C_{30}H_{45}NO_5Si$: C, 68.27; H, 8.59; N, 2.65. Found: C, 68.33; H, 8.68; N, 3.04.

24b. The same procedure was used to convert lactone 21b (5.5 g, 13.9 mmol)to acid 22b (white solid). This compound appeared slightly more prone to re-lactonization than 22a, reverting~30–40% to lactone upon standing at 0° C. for 45 days (solid phase).

The entire lot of 22b was converted to 23b as described for 22a→23a, and the product was deprotected to provide 24b without the additional 1 hour in the acidic solvent mixture. Chromatography as described gave 24b as a white foam.

$^1$H NMR: consistent with structure.

TLC (4% (v/v) MeOH/$CH_2Cl_2$), $R_f=0.49+0.56$.

Anal. Calc'd for $C_{30}H_{45}NO_5Si$: C, 68.27; H, 8.59; N, 2.65. Found: C, 68.53; H, 8.75; N, 2.87.

EXAMPLE 6

$N^\alpha$-[5-(t-Boc-amino)-4-hydroxy-6-phenyl-2-(phenylmethyl)hexanoyl]-(3S,4S)-statyl-L-leucinebenzylamide (26)

26a. Acid 24a (0.1 g, 0.19 mmol), Sta-Leu benzylamide hydrochloride (90 mg, 0.23 mmol), EDC (44 mg, 0.23 mmol), and HBT (31 mg, 0.23 mmol) were combined in dry, degassed DMF (0.5 mL) and stirred at room temperature. The pH of the mixture, measured by application of an aliquot to moistened colorpHast sticks (E. Merck), was adjusted to 9–9.5 with triethylamine, and the mixture was stirred 3 hours. The solvent was removed in vacuo and the residue was treated with 10% citric acid solution (10 mL) and extracted with EtOAc (2×5 mL). The combined organic layers were washed with citric acid (2×5 mL), saturated sodium bicarbonate (2×5 mL), and brine (1×5 mL), dried over sodium sulfate, filtered, and evaporated in vacuo to give 25a as a mixture of two diastereomers, ca. 3:1; $^1$H NMR: consistent with structure, two diastereomers observed.

Silylpeptide 25a (72 mg, 79 μmol) in THF (1 mL) was treated with tetrabutylammonium fluoride in THF (1 M, 0.24 mL, 240 μmol) and stirred at room temperature for 3 days after which time TLC (2% MeOH in CH$_2$Cl$_2$ showed the starting 25a to have been consumed. The mixture was evaporated in vacuo and chromatographed on silica gel (3% MeOH/CH$_2$Cl$_2$ elution) to give the isomer mixture 26a$_1$+26a$_2$ (2α,4R,5S and 2β,4R,5S).

$^1$H NMR: consistent with structure.
FABMS: (m/e) 772 (M), 773 (M+1), 774 (M+2).
HPLC: two diastereomers, 65% and 26%.
Calc'd for amino acid analysis (μmol/mg): Leu, 1.29.→Found: Leu, 1.31.

The mixture (~0 mg) was separated by preparative HPLC and the recovered fractions evaporated and rechromatographed on silica gel. Only the major component was obtained in sufficient quantity for characterization.

$^1$H NMR: consistent with structure.
FABMS:(m/e) 772 (M), 773 (M+1), 774 (M+2), 673 (M+2−Boc)/674/675.
HPLC: 99%.
Calc'd for amino acid analysis (μmol/mg): Leu, 1.29.→Found: Leu, 1.12.

26b. Acid 24b. (0.1 g, 0.19 mmol) was coupled to Sta-Leu benzylamide by the same procedure described for 24a, giving 25b as a mixture of two diastereomers, ca. 1.5:1.

$^1$H NMR: consistent with structure.
Silylpeptide 25b (137 mg, 150 μmol) in THF (1 mL) was treated with tetrabutylammonium fluoride in THF (1 M, 0.47 mL, 470 μmol) and stirred at room temperature for 3 days after which time TLC (2%, MeOH in CH$_2$Cl$_2$) showed the starting 25b to have been consumed. The mixture was evaporated in vacuo and chromatographed on silica gel (2% MeOH/CH$_2$Cl$_2$ elution) to give the separated diastereomers (2α and 2β) of the 4S,5S compound, 26b$_1$ and 26b$_2$.

26b$_1$. $^1$H NMR: consistent with structure.
HPLC 91% (contains 1.5% of isomer 26b$_2$). FABMS: (m/e) 795 (M+Na), 773 (M+1), 774 (M+2), 673 (M+2−Boc)/674/675. Calc'd for amino acid analysis (μmol/mg): Leu, 1.29. Found 1.22.

26b$_2$. NMR: consistent with structure.
HPLC: 89% (contains 3% of isomer 26b$_1$. Calc'd for amino acid analysis (μmol/mg): Leu, 1.29. Found: Leu, 1.31.

EXAMPLE 7

5-(1-Amino-2-phenylethyl)-3-phenylmethyldihydrofuran-2(3H)-one hydrochloride (27)

27a. Acid 24a (3.74 g, 7.1 mmol) was stirred in EtOAc (48 mL) immersed in an ice bath. HCl (g) was passed through the solution for 10 minutes and the mixture was stirred an additional 15 minutes in the cold. The solvent was removed under vacuum and the residue treated with EtOAc and evaporated (3 x). After standing under hexane (90 mL), the mixture was filtered to give the aminolactone hydrochloride 27a as a white solid.

$^1$H NMR; consistent with structure.
IR (KBr, cm$^{-1}$): 3200–3600 (br), 2450–3150 (br), 1775 (br s), 1495, 1165.
TLC (90:10:1:1, CH$_2$Cl$_2$:MeOH:HOAc:H$_2$O) single component, R$_f$0.45.
Anal. Calc'd for C$_{19}$H$_{21}$NO$_2$ HCl 0.1 C$_6$H$_{14}$: C, 69.14; H, 6.93; N, 4.11. Found: C, 69.05; H, 7.19; N, 401.

27b. Applied to acid 24b, this same procedure provided 27b (62%).

$^1$NMR: consistent with structure.
TLC (90:10:1:1,CH$_2$Cl$_2$:MeOH:HOAc:H$_2$O) single component, R$_f$=0.40.
Anal. Calc'd for C$_{19}$H$_{21}$NO$_2$ HCl: C, 68.77; H, 6.68; N, 4.22. Found: C, 68.81; H, 6.86; N, 4.30.

EXAMPLE 8

N$^α$-t-Boc-Phe-Phe-5-amino-4(hydroxy)-6-phenyl-2-(phenylmethyl)hexanoyl-Leu-Phe-amide Aminolactone hydrochloride 27b (1.5 g, 4.5 mmol) Boc-L-phenylalanine (1.32 g, 5.0 mmol), EDC (0.96 g, 5.0 mmol) and HBT (0.68 g, 5.0 mmol) were combined in dry, degassed DMF (26 mL) and stirred at room temperature. The pH of the mixture, as measured by spotting an aliquot on moistened colorpHast sticks (E. Merck), was raised to 9–9.5 by addition of triethylamine, and the mixture was stirred 2 hours, then refrigerated overnight.

The mixture was evaporated in vacuo and the residue treated with cold 10% citric acid (20 mL) and extracted with EtOAc (3×50 mL). The combined organic layers were washed with H$_2$O, dried over sodium sulfate, filtered and evaporated to dryness in vacuo. The residue was stirred in ethyl acetate (30 mL), immersed in an ice bath, and saturated with HCl (g) for 10 minutes. The mixture was evaporated several times from ethyl acetate, then from ether. The residue was coupled with Boc-L-phenylalanine using the procedure described above for 27b. Chromatography on silica gel (180:10:1 CH$_2$C$_1$:MeOH:HOAc elution) gave 28b as a white foam.

This material was dissolved in dioxane (40 mL), treated with H$_2$O (20 mL) and aqueous sodium hydroxide (3.55 mL of 1 M) and stirred at room temperature for 18 hours. The solvent was removed in vacuo and the residue dried under high vacuum for 18 hours. The resulting salt (2.3 g, 3.2 mmol) was treated with t-butyldimethylsilyl chloride (3.4 g, 22.5 mmol) and imidazole (3.6 g, 53 mmol) in dry DMF (40 mL) and stirred at room temperature. After 6 hours, additional portions of the silyl chloride (1.5 g) and imidazole (1.5 g) were added and the mixture stirred for 3 days. The mixture was evaporated in vacuo, treated with ice H$_2$O (100 mL), acidified to pH 4 with citric acid solution, and extracted with ethyl acetate (3×20 mL). The organic layers were washed with H$_2$O, dried over sodium sulfate, filtered, and evaporated in vacuo. The residue was chromatographed on silica gel (1% MeOH/CH to give the silyl ester as a white foam.

This solid was dissolved in THF (12 mL), treated with H$_2$O (4 mL) and glacial acetic acid (12 mL) and stirred at 3 hours at room temperature. The mixture was evaporated in vacuo, and the residue was diluted with H$_2$O, adjusted to pH~3(sodium bicarbonate+citric acid), and extracted with ethyl acetate (3×25 mL). The combined organic layers were washed with H$_2$O, dried over sodium sulfate, filtered and evaporated in vacuo. The residue was chromatographed on silica gel (1% to 5% MeOH in $CH_2Cl_2$) to give 29b as a white foam.

$^1H$ NMR: consistent with structure.

FABMS (m/e) 822 (M+1);

Acid 29b (0.8 g, 0.97 mmol), L-leucine benzylamide hydrochloride (0.33 g, 1.07 mmol), DCC (1 M in $CH_2Cl_2$, 1.02 mL, 1.02 mmol) and HBT hydrate (0.150 g, 1.02 mmol) were combined in dry DMF (12 mL) and the pH adjusted to 8.5 with triethylamine. The mixture was stirred 5 days at room temperature, then evaporated in vacuo. The residue was treated with dilute citric acid (10 mL) and extracted with ethyl acetate (3×15 mL). The combined organic layers were washed with citric acid (2×20 mL), sodium bicarbonate (2×20 mL), and brine, dried over potassium carbonate, filtered, and evaporated to dryness in vacuo.

A portion of the residue (0.95 g) was combined with 1 M tetrabutylammonium fluoride/THF (2.64 mL, 2.64 mmol) in 3 mL of THF and stirred at room temperature under nitrogen for 40 hours. The mixture was evaporated in vacuo and the residue chromatographed on silica gel (390:10:1 $CH_2Cl_2$:MeOH:concentrated $NH_3$ elution) to give the two diastereomers $30b_1$ and $30b_2$, in a series of mixed fractions ranging from 1:500 to 3:1 (total ~0.43 g). A portion of this material (0.3 g) was separated by preparative HPLC to give the two diastereomers $30b_1$ and $30b_2$, ($2\alpha$,4S,5S and $2\beta$,4S,5S) each as an amorphous white solid.

$30b_1$. $^1H$ NMR consistent with structure.
HPLC, 96.5%.
FABMS (m/e) 967 (M+1), 968 (M+2), 867 (M+2−Boc), 803, 703/4/5, 590.
Calc'd for amino acid analysis (μmol/mg): Leu, 1.03; Phe, 3.09. Found: Leu, 1.02; Phe, 3.04.

$30h_2$. $^1H$ NMR consistent with structure.
HPLC, 89.3%; contains 3% $30b_1$ and 4% de-Boc.
FABMS (m/e) 967 (M+1), 968 (M+2), 867 (M+2−Boc), 804, 704, 590.
Calc'd for amino acid analysis (μmol/mg): Leu, 1.03; Phe, 3.09. Found: Leu, 0.949; Phe, 2.89.

$30b_1$ and $30b_2$ are separated by TLC on silica gel, 80:10:1 $CH_2Cl_2$:MeOH:concentrated $NH_2$ elution: $30b_1$, $R_f$=0.48, $30b_2$=0.45.

Aminolactone hydrochloride 27a was coupled, deprotected, and coupled again with Boc-phenylalanine to give 28a as described for 28b. The resulting lactone was opened to the free acid, disilated, and monodesilated to give 29a, again as described for 29b. Chromatography provided a white solid:

$^1H$ NMR: consistent with structure
FABMS (m/e) 822 (M+1).

Acid 29a was coupled to L-leucine benzylamide and the product desilated to give $30a_1$ and $30a_2$ using the procedure described for conversion of 29b to $30b_1$ and $30b_2$ except that the tetrabutylammonium fluoride desilation required 3 days to proceed to completion. A portion (0.26 g) of the chromatographed mixture of diastereomers was separated by preparative HPLC to give $30a_1$ and $30a_2$ ($2\alpha$,4R,5S and $2\beta$,4R,5S) as amorphous white solids, along with considerable mixed material.

$30a_1$. $^1H$ NMR consistent with structure.
HPLC 96.6% (contains 1.1% of $30a_2$);
FABMS (m/e) 967 (M+1), 968 (M+2), 867 (M+2−Boc), 803, 703/4/5, 590.
Calc'd for amino acid analysis (μmol/mg): Leu, 1.03; Phe, 3.09. Found: Leu, 1.06; Phe, 3.23.

$30a_2$. $^1H$ NMR consistent with structure,
HPLC 85% (contains 11% N-de-Boc'd compound);
FABMS (m/e) 967 (M+1), 968 (M+2), 867 (M+2−Boc), 803, 703/4/5, 590.
Amino acid analysis: Calcd (μmol/mg): Leu, 1.03; Phe, 3.09. Found: Leu, 1.03; Phe, 2.96.

EXAMPLE 9

$N^\alpha$-[5-(t-Boc-amino)-4-hydroxy-6-phenyl-2-(phenylmethyl)hexanoyl]-(3S,4S)-4-amino-5-cyclohexyl-3-hydroxypentanoyl-L-leucyl-m-aminomethylbenzylamide (33)

Acid 24a (0.56 g, 1.06 mmol), ACHPA-L-Leu-m-aminomethylbenzylamide hydrochloride (0.5 g, 0.86 mmol), EDC (0.166 g, 0.86 mmol) and HBT (0.116 g, 0.86 mmol) were combined in dry, degassed DMF (2 mL), the pH was adjusted to 9–9.5 with triethylamine, and the mixture was stirred 6 hours at room temperature. The reaction was quenched in a cold pH4 buffer (50 mL) prepared by addition of sodium bicarbonate to a 10% citric acid solution, and extracted with ethyl acetate (3×15 mL). The organic layers were combined, washed with the buffer (1×20 mL), with saturated sodium bicarbonate (1×20 mL), and with brine (1×20 mL), dried over sodium sulfate, filtered and evaporated in vacuo to give a white foam. Chromatography on silica gel (2% MeOH/$CH_2Cl_2$ elution) gave the two separated diastereomers $32a_1$ and $32a_2$ as white amorphous solids. Flushing with 10% MeOH/$CH_2Cl_2$ provided an additional 0.22 g of material consisting mainly of $32a_1$ which was not processed further.

$32a_1$. $^1H$ NMR consistent with structure.
FDMS (m/e) 1052 (M+1), 1053 (M+2), 994, 960, 832.

$32a_2$. $^1H$ NMR consistent with structure.
FDMS (m/e) 1052 (M+1), 1053 (M+2), 994, 960, 832.

Acid 24b was coupled to ACHPA-L-Leu-m-aminomethylbenzylamide by the same procedure. Chromatography provided $32b_1$ and $32b_2$ as amorphous white solids.

$32b_1$. $^1H$ NMR consistent with structure.
FDMS (m/e) 1052 (M+1), 1053 (M+2), 953, 952.

$32b_2$. 1H NMR consistent with structure.
FDMS (m/e) 1052 (M+1), 1053 (M+2), 994, 960, 935.

Each of the four individual diastereomers of 32 was detrifluoroacetylated by stirring 6 days at room temperature in 5 mL of MeOH containing 5 mL of a 7% solution of potassium carbonate in 40% aqueous methanol. The reactions each showed a single product on TLC (90:10:1:1 $CH_2Cl_2$:MeOH:HOAc:$H_2O$, silica gel, PMA stain). Each reaction was evaporated in vacuo, and the residue treated with $H_2O$ (3 mL) and extracted with ethyl acetate (3×5 mL). The combined organic layers were dried over potassium carbonate, filtered and evaporated to give the deprotected amines.

These amines were each desilated by stirring for 24 hours at room temperature with a 3-fold molar excess of tetrabutylammonium fluoride (1 M in THF). Each reaction mixture was evaporated in vacuo and the residue chromatographed on silica gel (170:10:1 $CH_2Cl_2$:MeOH:concentrated $NH_3$ elution) to give the final products $33a_1$, $a_2$, $b_1$, and $b_2$. ($2\alpha$, 4R,5S; $2\beta$,4R,5S; $2\alpha$, 4S,5S; and $2\beta$, 4S,5S respectively.)

33a₁. ¹H NMR consistent with structure. HPLC 92.5% (contains 1.6% of 33a₂); FABMS (m/e) 842 (M+1), 843 (M+2), 844 (M+3), 742 (M+2−Boc).

Calc'd for amino acid analysis (μmol/mg): Leu, 1.19. Found: Leu, 1.07.

33a₂. 360 MHz ¹H NMR consistent with structure. HPLC 97.3% (contains 0.75% of 33a₁.

FABMS (m/e) 842 (M+1), 843 (M+2), 844 (M+3), 742 (M+2−Boc).

Calc'd for amino acid analysis (μmol/mg): Leu, 1.19. Found: Leu, 1.07.

33b₁. ¹H NMR consistent with structure. HPLC, 94.2% (contains 3.1% of 33b₂); FABMS (m/e) 842 (M+1), 843 (M+2), 844 (M+3), 742 (M+2−Boc).

Calc'd for amino acid analysis (μmol/mg): Leu, 1.19. Found: Leu, 1.04.

33b₂. ¹H NMR consistent with structure. HPLC, 85.7% (contains 5.5% of 33b₁); FABMS (m/e) 842 (M+1), 843 (M+2), 844 (M+3), 742 (M+2−Boc).

Calc'd for amino acid analysis (μmol/mg): Leu, 1.19. Found: Leu, 0.99.

EXAMPLE 10

3-(t-Boc-amino)-2-hydroxy-4-phenyl-1-(1-phenylethylamino)butane (34)

34a. Epoxide 16a (52 mg, 0.2 mmol) and d-(+)-(R)-α-methylbenzylamine (27 mg, 0.22 mmol) were combined in 2-propanol (1 mL) and heated for 5 hours in an oil bath thermostatted at 70° C. The mixture was cooled and evaporated in vacuo. The residue was chromatographed on silica gel (5% methanol in methylene chloride) and the combined product fractions evaporated in vacuo to give 34a.

¹H NMR consistent with structure, one diastereomer seen.

TLC (4% MeOH/CH₂Cl₂, single component, R_f=0.27).

Anal. Calc'd for C₂₃H₃₂N₂O₃·0.3 H₂O: C, 70.84; H, 8.43; N, 7.18. Found: C, 70.54; H, 8.45; N, 7.14.

34a+d. Repetition of the same procedure using achiral epoxide 16a+d (1:1) provided the corresponding carbinolamines 34a+d. ¹H NMR consistent with structure, two diastereomers seen.

TLC (4% MeOH/CH₂Cl₂, single component, R_f=0.27).

Anal. Calc'd for C₂₃H₃₂N₂O₃ 0.3 H₂O: C, 70.84; H, 8.43; N, 7.18. Found: C, 70.67; H, 8.33; N, 7.51.

Claims to the invention follow.
What is claimed is:
1. A compound of the formula:

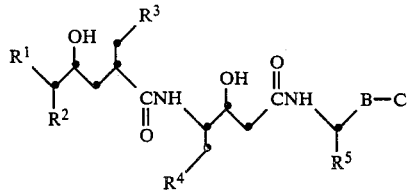

and its pharmaceutically acceptable salts wherein:
(i) R¹ is A—B'—B'—D'—NH wherein:
   A is hydrogen;

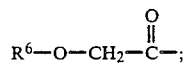

-continued
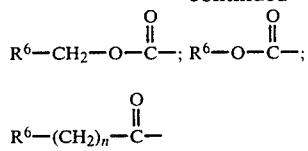

wherein n is 0−5; or

where R⁶ is hydrogen;
C₃₋₆ alkyl; C₃₋₇ cycloalkyl; phenyl; or phenyl mono-substituted with a member selected from the group consisting of methyl, trifluoromethyl, hydroxy, methoxy, fluoro, chloro, bromo, and iodo;
B' is absent; glycyl; or

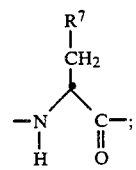

D' is absent; or

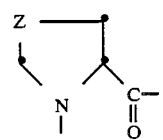

where Z is (CH₂)ₙ and n is 1 or 2; or —S—;
R⁷ is hydrogen; C₁₋₄ alkyl; hydroxy C₁₋₄ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine C₂₋₄ alkyl; guanidyl C₂₋₃ alkyl; or methylthiomethyl; and
R² is CH₂R⁸ wherein
   R⁸ is hydrogen C₁₋₄; alkyl; phenyl; phenyl mono-substituted with a member selected from the group consisting of methyl, trifluoromethyl, hydroxy, methoxy, fluoro, chloro, bromo, and iodo; or indolyl; and
(ii) R¹ and R² are the same or different and are hydrogen; Y—(CH₂)ₙ— or Y—(CH₂)ₘ—CH═CH—(CH₂)ₚ— where Y is hydrogen; aryl; aryl substituted with up to five members independently selected from the group consisting of C₁₋₈ alkyl, trifluoromethyl, hydroxy, C₁₋₄ alkoxy, and halo; n is 0 to 5; m is 0 to 2; and p is 0 to 2; and
R³ is hydrogen; C₁₋₄ alkyl; hydroxy C₁₋₄ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine C₂₋₄ alkyl; guanidyl C₂₋₃ alkyl; or methylthiomethyl;
R⁴ is C₁–C₄ branched or linear alkyl, C₃–C₆ cycloalkyl, phenyl or monosubstituted phenyl wherein the substituent is OH, Cl, F, Br, CH₃, CF₃, I or OCH₃, R⁵ is hydrogen or

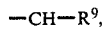,

wherein $R_a^9$ and $R_b^9$ are independently selected from hydrogen, $C_1$-$C_4$ alkyl, hydroxy, phenyl or $C_3$-$C_7$ cycloalkyl;

B-C is

wherein $R^{10}$ is selected from (a)

B''  V wherein
B'' is OR; NHR; or NR₂, where each R may be the same or different and is hydrogen or $C_{1-4}$ alkyl;

(b)

B''—E  VI wherein
B'' is absent; glycyl; or

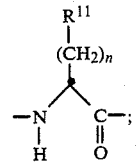

wherein n is 1 or 2; or —S—;
$R^{11}$ is hydrogen; $C_{1-4}$ alkyl; hydroxy $C_{1-4}$ alkyl; phenyl; phenyl mono-substituted with a member selected from the group consisting of methyl, trifluoromethyl, hydroxy, methoxy, fluoro, chloro, bromo, and iodo; indolyl; 4-imidazolyl; amine $C_{2-4}$ alkyl; guanidyl $C_{2-3}$ alkyl; or methylthiomethyl; and
E is OR; NHR, or N(R)₂, where each R may be the same or different and is hydrogen or $C_{1-4}$ alkyl; and (c)

B°—D—E  VII wherein
B° is (1) —Y—(CH₂)ₙ—R¹² where Y is —NH— or —O—; n is 0 to 5; and $R^{12}$ is hydrogen; hydroxy; $C_{1-4}$alkyl; $C_{3-7}$cycloalkyl; aryl; aryl substituted with up to five members independently selected from the group consisting of $C_{1-6}$alkyl, trifluoromethyl, hydroxy, $C_{1-4}$alkoxy, amino, mono- or di- $C_{104}$ alkylamino, and halo; amino; mono-, di-, or tri-$C_{1-4}$alkylamino; guanidyl; heterocyclic; or heterocyclic substituted with up to five members independently selected from the group consisting of $C_{1-6}$alkyl, hydroxy, trifluoromethyl, $C_{1-4}$alkoxy, halo, aryl, aryl $C_{1-4}$alkyl, amino, and mono- or di-$C_{1-4}$alkylamino; (2)

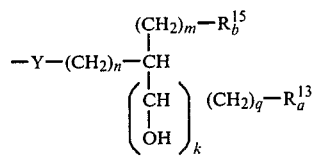

where Y is as defined above; n is 0 or 1; k is 0 or 1; q is 1 to 4; m is 1 to 4; and $R_a^{19}$ and $R_b^{19}$ may be the same or different and have the same meaning as $R^{12}$ above and $R_a^{13}$ may additionally be

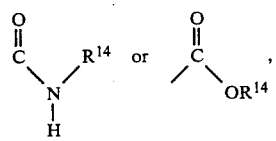

where $R^{14}$ is hydrogen or $C_{1-3}$alkyl; (3)

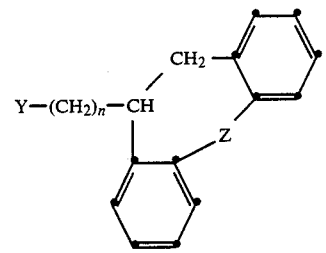

where Y is as defined above; n is 0 or 1; and Z is (a)

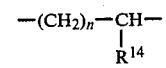

where n is 0 or 1; and $R^{14}$ is as defined above; or (b)

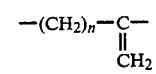

where n is 0 or 1; or (4)

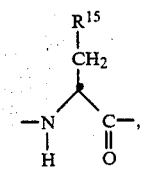

wherein $R^{15}$ has the same meaning as $R^4$ above;

D is absent; glycyl; sarcosyl; or

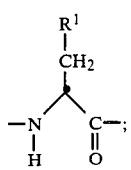

and

E is absent; OR; NHR; or N(R)₂' where R may be the same or different and is hydrogen or C₁₋₄alkyl; or (d)

—E—   VIII wherein:

E is (1) —Y—(CH₂)ₙ—R¹⁶ where Y is —NH— or —O—; n is 0 to 5; and R¹⁶ is hydrogen; C₁₋₃alkyl; C₃₋₇cycloalkyl; naphthyl; phenyl; phenyl substituted with up to five members independently selected from the group consisting of methyl, trifluoromethyl, hydroxyl, methoxy, amino, fluoro, chloro, bromo, and iodo; imidazolyl; pyridyl; pyrryl; hydroxyl; amino; C₁₋₄alkyl mono-, di-, or tri-substituted amino; guanidyl; piperidyl; tetrahydropyrryl; or N-substituted piperidyl or tetrahydropyrryl where the N-substituent is a member selected from the group consisting of hydrogen, C₁₋₆alkyl, C₁₋₆hydroxyalkyl, phenyl, benzyl, naphthyl, and naphthylmethyl; (2)

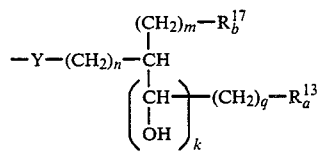

where Y is as defined above; n is 0 or 1; k is 0 or 1; q is 1 to 4; m is 1 to 4; and Rₐ¹⁷ and Rᵦ¹⁷ and may be the same or different and have the same meaning as R¹⁶ above; or (3)

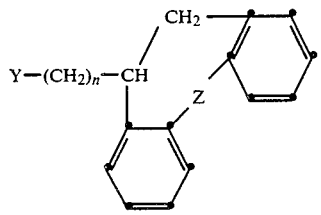

where Y is as defined above; n is 0 or 1; and Z is (a)

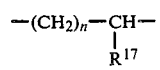

where n is 0 or 1; and R¹⁷ is hydrogen or C₁₋₃alkyl; or (b)

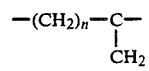

where n is 0 or 1.

2. A compound of claim 1 selected from:
(a) Nα-[5-(t-Boc-amino)-4-hydroxy-6-phenyl-2-(phenylmethyl)hexanoyl]-(3S,4S)-4-amino-5-cyclohexyl-3-hydroxypentanoyl-L-leucyl-m-aminomethylbenzylamide, and
(b) Nα-[5-(t-Boc-amino)-4-hydroxy-6-phenyl-2-(phenylmethyl)hexanoyl]-(3S,4S)-statyl-L-leucinebenzylamide.

3. The (a) compound of claim 2.

4. The compound of claim 3 having the 2R,4S,5S configuration in the 5-(t-Boc)-amino-4-hydroxy-6-phenyl-2-(phenylmethyl)hexanoyl unit.

5. The compound of claim 3 having the 2S,4S,5S configuration in the 5-(t-Boc)-amino-4-hydroxy-6-phenyl-2-(phenylmethyl)hexanoyl unit.

6. The compound of claim 3 having the 2R,4R,5S configuration in the 5-(t-Boc)-amino-4-hydroxy-6-phenyl-2(phenylmethyl)hexanoyl unit.

7. The compound of claim 3 having the 2S,4R,5S configuration in the 5-(t-Boc)-amino-4-hydroxy-6-phenyl-2-(phenylmethyl)hexanoyl unit.

8. The (b) compound of claim 2.

9. The compound of claim 8 having the 2R,4R,5S configuration in the 5-(t-Boc-amino)-4-hydroxy-6-phenyl-2-(phenyl(methyl)hexanoyl unit.

10. The compound of claim 8 having the 2S,4R,5S configuration in the 5-(t-Boc-amino)-4-hydroxy-6-phenyl-2-phenylmethylhexanoyl unit.

11. The compound of claim 8 having the 2R,4S,5S configuration in the 5-(t-Boc-amino)-4-hydroxy-6-phenyl-2-phenylmethylhexanoyl unit.

12. The compound of claim 8 having the 2S,4S,5S configuration in the 5-(t-Boc-amino)-4-hydroxy-6-phenyl-2-phenylmethyl hexanoyl unit.

13. A composition for treating renin-associated hypertension or renin-associated hyperaldosteronism comprising a renin-inhibitory amount of a compound according to claim 1 and a carrier.

* * * * *

UNITED STATES PATENT AND TRADEMARK OFFICE
CERTIFICATE OF CORRECTION

PATENT NO. : 4,665,055
DATED : May 12, 1987
INVENTOR(S) : B. E. Evans

It is certified that error appears in the above—identified patent and that said Letters Patent is hereby corrected as shown below:

In the Specification:

Column 18, line 6, after "published" and before "is converted" please amend "methods, 3" to -- methods, $^3$ --.

Column 19, line 58, after "diastereomer crop (16", and before "+d", please add --a--

Column 23, line 24, after "The mixture", amend (~0mg) to--(~40mg)--

Column 24, line 60, after "1% MeOH/", amend "CH", to--$CH_2Cl_2$)--

Column 29, line 63, after "or di-", and before "alkylamino", amend "$C_{104}$", to--$C_{1-4}$--

Column 31, line 61, after "$R_b^{17}$", and before "may be the", please remove "and"

Signed and Sealed this

First Day of December, 1987

*Attest:*

DONALD J. QUIGG

*Attesting Officer*    *Commissioner of Patents and Trademarks*